United States Patent [19]
de Lacharriere et al.

[11] Patent Number: 5,932,215
[45] Date of Patent: Aug. 3, 1999

[54] THERAPEUTIC/COSMETIC COMPOSITIONS COMPRISING CGRP ANTAGONISTS FOR TREATING SKIN REDNESS/ROSACEA/DISCRETE ERYTHEMA

[75] Inventors: Olivier de Lacharriere, Paris; Lionel Breton, Versailles, both of France

[73] Assignee: Societe L'Oreal S.A., Paris, France

[21] Appl. No.: 08/620,806

[22] Filed: Mar. 28, 1996

[30] Foreign Application Priority Data

Mar. 28, 1995 [FR] France ................................. 95-03628

[51] Int. Cl.$^6$ ................. A61K 39/395; A61K 39/00; A61K 6/00; A01N 37/18
[52] U.S. Cl. ..................... 424/158.1; 424/130.1; 424/133.1; 424/145.1; 424/185.1; 424/198.1; 424/809; 424/401; 514/2
[58] Field of Search .............. 424/401, 130.1, 424/133.1, 145.1, 158.1, 185.1, 198.1, 809; 514/2

[56] References Cited

U.S. PATENT DOCUMENTS

| | | | |
|---|---|---|---|
| 5,164,372 | 11/1992 | Matsuo et al. | 514/19 |
| 5,445,823 | 8/1995 | Hall et al. | 424/401 |
| 5,585,385 | 12/1996 | Natsugari et al. | 514/300 |
| 5,658,581 | 8/1997 | Lacharriere et al. | 424/401 |
| 5,679,360 | 10/1997 | Lacharriere et al. | 424/401 |
| 5,730,998 | 3/1998 | Lacharriere et al. | 424/443 |
| 5,744,156 | 4/1998 | Lacharriere et al. | 424/445 |
| 5,824,650 | 10/1998 | Lacharriere et al. | 514/5 |
| 5,869,068 | 2/1999 | Lacharriere et al. | 424/401 |

FOREIGN PATENT DOCUMENTS

93/21911  11/1993  WIPO .

OTHER PUBLICATIONS

Bartho et al. 1991 Neuroscience Letters 129 pp. 156–159, Jan. 1, 1991.
Brain et al 1986 J Invest Dermatol 87 pp. 533–536, Jan. 1, 1986.
Fuller et al. 1987 Br J Pharmacol 92 pp. 781–788, Jan. 1, 1987.
Herbert et al. 1994 Br J Pharmacol 111 pp. 681–686, Jan. 1, 1994.
Hua et al. 1993 J Neurosci 13 (5) pp. 1947–53, May 1, 1993.
Peskar et al. 1993 Eur J Pharmacology 250 pp. 201–203, Jan. 1, 1993.
Shaw et al. 1992 Br J Pharmacol 106 pp. 196–198, Jan. 1, 1992.
Tan et al. 1995 Clinical Science 89 pp. 565–5733, Dec. 1, 1995.
Wallengren et al. 1987 Eur J Pharmacol 143 pp. 267–273, Nov. 10, 1987.
Neuroscience, vol. 48, No. 4, Jun. 1992, pp. 963–968, T.L. Buckley, et al., 'The Partial Inhibition of Inflammatory Responses Induced by a Capsaicin Using the Fab Fragment of a Selective Calcitonin Gene–Related Peptide Antiserum in Rabbit Skin.'
British Journal of Pharmacology, vol. 110, No. 2, 1993, pp. 772–776, K. Jane Escott, et al., 'Effect of Calcitonin Gene–Related Peptide Antagonist (CGRP 8–37) on Skin Vasodilatation and Oedema Induced by Stimulation of the Rat Saphenous Nerve.'
British Journal of Pharmacology, vol. 104, No. 3, Nov. 1991, pp. 738–742, S.R. Hughes, et al., 'A Calcitonin Gene–Related Peptide (CGRP) Antagonist (CGRP 8–37) Inhibits Microvascular Responses Induced by CGRP and Capsaicin in Skin.'
Neuroscience Letters, vol. 102, No. 2.3, Jul. 31, 1989, pp. 257–260, S.M. Louis, et al., 'Antibodies to Calcitonin Gene–Related Peptide Reduce Inflammation Induced by Topical Mustard Oil But Not That Due to Carrageenin in the Rat.'

*Primary Examiner*—Frank C. Eisenschenk
*Assistant Examiner*—Mary K. Zeman
*Attorney, Agent, or Firm*—Burns, Doane, Swecker & Mathis, L.L.P.

[57] ABSTRACT

Skin redness, rosacea and/or discreet erythema afflicting a mammalian, notably human patient, are therapeutically treated by administrating to such patient a therapeutically/cosmetically effective amount of at least one CGRP antagonist, advantageously in combinatory immixture with at least one antagonist of a neuropeptide other than CGRP, e.g., a substance P antagonist, and/or at least one inflammation mediator antagonist.

22 Claims, No Drawings

THERAPEUTIC/COSMETIC COMPOSITIONS COMPRISING CGRP ANTAGONISTS FOR TREATING SKIN REDNESS/ROSACEA/DISCRETE ERYTHEMA

CROSS-REFERENCE TO COMPANION APPLICATIONS

Copending applications Ser. No. 08/592,529 [Attorney Docket No. 016800-066], filed Jan. 26, 1996, and Ser. No. 08/623,576, [Attorney Docket No. 016800-075] and Ser. No. 08/620,805, [Attorney Docket No. 016800-077], both filed concurrently herewith, and each assigned to the assignee hereof.

BACKGROUND OF THE INVENTION

1. Technical Field of the Invention

The present invention relates to the formulation of an antagonist of CGRP (peptide derived from the calcitonin gene: Calcitonin Gene Related Peptide, or "CGRP") into cosmetic/pharmaceutical/dermatological compositions, in particular for topical application, for treating rosacea and/or discreet erythema.

More especially, this invention relates to the topical, ingestible or injectable treatment of rosacea or discreet erythema.

2. Description of the Prior Art

It is known to this art that rosacea is a skin affliction characterized by erythema of the face, predominantly on the cheeks, the forehead and the nose, hyperseborrhoea of the face on the forehead, the nose and the cheeks, and an infectious component manifesting acneiform pustules.

Moreover, these indications are associated with a neurogenic component, namely, a cutaneous hyperreactivity of the skin of the face and of the neck, characterized by the appearance of redness and subjective sensations of the itching or pruritus type, sensations of burning or of heating, sensations of stinging, tingling, discomfort, tightness, etc.

These signs of hyperreactivity may be triggered by very varied factors such as the intake of food or of hot or alcoholic drinks, by rapid temperature variations, by heat and in particular exposure to ultraviolet or to infrared irradiation, by a low relative humidity, by exposure of the skin to strong winds or to currents of air (conditioned air, fans and blowing machines), by the application of surfactants, irritant dermatological topical agents (retinoids, benzoyl peroxide, alpha-hydroxy acids, etc.), or the use of certain cosmetics, even when these are themselves not recognized as being particularly irritating.

Hitherto, the mechanism for triggering these indications was very poorly understood and rosacea was treated with active agents such as anti-seborrhoeic agents and anti-infection agents, for example benzoyl peroxide, retinoic acid, metronidazole or cyclins, which act on infection and hyperseborrhoea but do not permit the neurogenic component of this affliction, and in particular hyperreactivity of the skin and redness, to be treated.

Similarly, hitherto no treatment existed for the redness which develops in discreet erythema. This latter affliction occurs at times of emotion and is characterized by redness of the face and neckline, which possibly may be accompanied by pruritus (itching). This condition is very irritating for individuals suffering therefrom, and to date it could only be treated by beta-blockers, powerful drugs used for treating hypertension and exhibiting many contra-indications.

Thus, serious need continues to exist in this art for an effective treatment of skin redness and of the state of hyperreactivity of skin affected by rosacea or discreet erythema.

SUMMARY OF THE INVENTION

A major object of the present invention is the administration of one or more CGRP antagonists to a mammalian, notably human patient, for treating the disease states indicated above.

CGRP is a polypeptide chemical species produced and released by a nerve ending. CGRP is involved, in particular, in respiratory and inflammatory diseases, in allergic diseases and in certain dermatological diseases such as eczema and prurigo.

However, to date it was not envisaged to use CGRP antagonists for treating skin redness of neurogenous origin.

It is now unexpectedly been determined that CGRP antagonists are useful for eliciting a preventive and/or curative effect on skin redness.

Thus, the present invention features the formulation of at least one CGRP antagonist into a cosmetic, pharmaceutical or dermatological composition, for treating skin redness of neurogenic origin, in particular due to the release of neuropeptides.

DETAILED DESCRIPTION OF BEST MODE AND SPECIFIC/PREFERRED EMBODIMENTS OF THE INVENTION

More particularly according to the present invention, at least one CGRP antagonist is formulated into a cosmetic, pharmaceutical or dermatological composition for treating rosacea and/or discreet erythema.

The administration of compositions containing one or more CGRP antagonists permits eliciting a marked decrease or even complete disappearance of skin redness, which is manifested both in rosacea and in discreet erythema.

The CGRP antagonist thus acts on the neurogenic component of these disease states, for which no treatment hitherto existed, and thereby reinforces the effectiveness of the known active agents for treating their infectious component, in particular in the case of rosacea.

The compositions of the invention may be administered either via a local route, namely, topically or by subcutaneous and/or intradermal injection, or via a systemic or general route, namely, orally and/or by intramuscular injection. Preferably, they are topically administered.

The present invention accordingly features a regimen for the cosmetic, pharmaceutical and/or dermatological treatment of skin redness of neurogenic origin, comprising topically applying a composition containing at least one CGRP antagonist, in a cosmetically, pharmaceutically and/or dermatologically acceptable medium (vehicle, diluent or carrier), to the skin, to the scalp and/or to the mucous membranes.

This invention also features a regimen for the cosmetic, pharmaceutical and/or dermatological treatment of rosacea and/or discreet erythema, comprising topically applying a composition containing at least one CGRP antagonist, in a cosmetically, pharmaceutically and/or dermatologically acceptable medium, to the skin, to the scalp and/or to the mucous membranes.

The subject compositions for topical application comprise a cosmetically, pharmaceutically or dermatologically acceptable medium (vehicle, diluent or carrier), namely, a medium which is compatible with the skin, the nails, the mucous membranes, tissues and the hair. The compositions containing the CGRP antagonist or antagonists are advantageously applied topically to the face, the neck, the hair, the mucous membranes and the nails, major folds, or any other body skin region.

By "CGRP antagonist" is intended any molecule, whether organic or inorganic, effecting inhibition of the receptor binding of CGRP or of effecting inhibition of the synthesis and/or release of CGRP by sensitive nerve fibers.

In order for a chemical species to be recognized as a CGRP antagonist, it must in particular satisfy the following characteristic: it must have a CGRP antagonist pharmacological activity, i.e., induce a coherent pharmacological response, in particular in one of the following tests:

(a) the antagonist species must reduce the vasodilation induced by capsaicin and/or (b) the antagonist species must induce an inhibition of the release of CGRP by sensitive nerve fibers and/or (c) the antagonist species must induce an inhibition of the contraction of vas deferens smooth muscle induced by CGRP.

In addition, the antagonist must have an affinity for the CGRP receptors.

CGRP 8-37, and anti-CGRP antibodies are suitable for use according to the invention, for example, as a CGRP antagonist.

In the compositions according to the invention, the CGRP antagonist is preferably employed in an amount ranging from 0.000001% to 10% by weight relative to the total weight of the composition, and in particular in an amount ranging from 0.0001% to 5% by weight relative to the total weight of the composition.

The CGRP antagonist may advantageously be combined with one or more antagonists of another neuropeptide such as substance P antagonists and/or one or more inflammation mediator antagonists such as histamine antagonists, interleukin 1 (IL1) antagonists and Tumor Necrosis Factor alpha (TNFα) antagonists.

Thus, the present invention also features cosmetic/pharmaceutical/dermatological compositions for treating skin redness, comprising, in a cosmetically, pharmaceutically and/or dermatologically acceptable medium (vehicle, diluent or carrier), at least one CGRP antagonist and at least one antagonist of another neuropeptide and/or at least one inflammation mediator antagonist.

The antagonist of a neuropeptide other than CGRP is preferably a substance P antagonist.

Substance P is a polypeptide chemical species produced and released by a nerve ending. It is a member of the family of tachykinins which originate from free nerve endings in the epidermis and the dermis. Substance P is involved, in particular, in the transmission of pain and in central nervous system disorders such as anxiety and schizophrenia, in respiratory and inflammatory diseases, in gastro-intestinal diseases, in rheumatic diseases and in certain dermatological diseases such as eczema, psoriasis, urticaria and contact dermatitis.

For a chemical entity to be recognized as a substance P antagonist, it must satisfy the following characteristic: it must have a substance P antagonist pharmacological activity, namely, induce a coherent pharmacological response in at least one of the following two tests:

(i) the antagonist species must decrease the extravasation of the plasma across the vascular wall induced by capsaicin or by antidromic nerve stimulation, or, alternatively, (ii) the antagonist species must elicit an inhibition of the contraction of smooth muscles induced by the administration of substance P.

The substance P antagonist may also elicit selective affinity for the tachykinin NK1 receptors.

The substance P antagonist of the invention may be functional or receptorial, i.e., inhibit the synthesis and/or the release of substance P, or prevent its binding and/or modify its action.

The substance P antagonist is preferably a substance P receptor antagonist.

The substance P antagonist of the invention may be selected from among peptides or non-peptide derivatives, and more preferably those comprising a nitrogen-containing, sulfur-containing or oxygen-containing heterocycle, or nitrogen-containing compounds containing a nitrogen atom bonded directly or indirectly to a benzene ring.

Sendide and spantide II are exemplary substance P antagonist peptides.

Peptides which are well suited consistent with this invention are those described, for example, in U.S. Pat. No. 4,472,305, U.S. Pat. No. 4,839,465, EP-A-101,929, EP-A-333,174, EP-A-336,230, EP-A-394,989, EP-A-443,132, EP-A-498,069, EP-A-515,681, EP-A-517,589, WO-A-92/22569 and GB-A-2,216,529.

The non-peptide substance P antagonists which are suitable according to the invention include, in particular, heterocyclic compounds, in particular sulfur-containing, nitrogen-containing or oxygen-containing heterocyclic compounds or compounds comprising a nitrogen atom bonded directly or indirectly to a benzene ring.

Exemplary heterocyclic compounds according to the invention are those described in EP-A-360,390, EP-A-429,366, EP-A-430,771, EP-A-499,313, EP-A-514,273, EP-A-514,274, EP-A-514,275, EP-A-514,276, EP-A-520,555, EP-A-528,495, EP-A-532,456, EP-A-545,478, EP-A-558,156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01160, WO-A-93/01170, WO-A-93/06099, WO-A-93/09116 and WO-A-94/08997. In particular, the compound comprising at least one nitrogen-containing heterocycle is advantageously a 2-tricyclyl-2-aminoethane derivative, a spirolactam derivative, a quinuclidine derivative, an azacyclic derivative, an aminopyrrolidine derivative, a piperidine derivative, an aminoazaheterocycle or an isoindole derivative.

Exemplary compounds containing a nitrogen atom bonded directly or indirectly to a benzene ring include those described in EP-A-522,808 and WO-A-93/01165.

And exemplary inflammation mediator antagonists according to the invention include diethylenediamine derivatives such as cinnarizine and cyclizine; aminopropane derivatives (dexchlorpheniramine, triprolidine); phenothiazine derivatives (alimemazine, promethazine); auranofin; lisophyline; A802715; sulfasalazine; cetirizine HCl; loratidine; esbatine; setastine HCl.

By way of example, the substance P antagonists and the inflammation mediator antagonists may be formulated in an amount constituting from 0.000001% to 10% of the total weight of the composition and, preferably, from 0.0001% to 5%.

The compositions according to the invention may comprise all pharmaceutical forms normally utilized according to the route of administration (injection, oral or topical route).

For topical applications, the subject compositions may be formulated into any pharmaceutical form normally employed for such an application, in particular in the form of aqueous, aqueous/alcoholic or oily solutions, dispersions of lotion or serum type, aqueous, anhydrous or lipophilic gels, emulsions of liquid or semi-liquid consistency of the milk type, obtained by dispersion of a fatty phase in an aqueous phase (O/W) or conversely (W/O), or suspensions or emulsions of runny, semi-solid or solid consistency of the cream or gel type, or alternatively microemulsions, microcapsules, microparticles, or vesicle dispersions of ionic and/or nonionic type. These compositions are formulated according to conventional techniques.

They may also be used for the hair in the form of aqueous, alcoholic or aqueous/alcoholic solutions, or in the form of creams, gels, emulsions or foams or alternatively in the form of aerosol compositions also containing a propellant under pressure.

The injectable compositions may be formulated as an aqueous or oily lotion, or in the form of a serum.

The compositions for oral administration may be formulated as wafer capsules, gelatin capsules, syrups or tablets.

The amounts of the various constituents of the compositions according to the invention are those conventionally used in the fields under consideration.

These compositions typically constitute protective, treatment or care creams for the face, for the hands, for the feet, for the major anatomical folds or for the body, body milks for protection or care, lotions, gels or foams for care of the skin and the mucous membranes, such as cleansing or disinfecting lotions, compositions for the bath, or compositions containing a bactericidal agent.

The subject compositions may also be formulated as solid preparations constituting soaps or cleansing bars.

The cosmetic treatments according to the invention may be carried out, in particular, by applying the cosmetic or hygienic compositions as described above, according to the usual techniques for administering these compositions. For example: application of creams, gels, sera, lotions and milks to the skin, the scalp and/or the mucous membranes.

When the compositions of the invention are formulated as an emulsion, the proportion of the fatty phase advantageously ranges from 5% to 80% by weight, and preferably from 5% to 50% by weight, relative to the total weight of the composition. The oils, the emulsifying agents and the coemulsifying agents employed in the compositions in emulsion form are selected from among those used conventionally in the cosmetics field. The emulsifying agent and the coemulsifying agent are advantageously present in the compositions, in a proportion ranging from 0.3% to 30% by weight, and preferably from 0.5 to 20% by weight, relative to the total weight of the composition. The emulsion may also contain lipid vesicles.

When the compositions of the invention comprise an oily gel or solution, the fatty phase may constitute more than 90% of the total weight of the composition.

In a known manner, the cosmetic, pharmaceutical or dermatological compositions of the invention may also contain additives and adjuvants common in such fields, such as hydrophilic or lipophilic gelling agents, hydrophilic or lipophilic active agents, preservatives, antioxidants, solvents, fragrances, fillers, sunscreens, bactericides, odor absorbers and dyestuffs and colorants. The amounts of these various additives and adjuvants are those used conventionally in the fields under consideration and range, for example, from 0.01% to 20% of the total weight of the composition. Depending on their particular nature, these additives and adjuvants may be introduced into the fatty phase, into the aqueous phase and/or into lipid spherules.

Exemplary oils which are suitable for the compositions of the invention include mineral oils (liquid petrolatum), plant oils (liquid fraction of karite butter and sunflower oil), animal oils (perhydrosqualene), synthetic oils (purcellin oil), silicone oils (cyclomethicone) and fluoro oils (perfluoropolyethers). Fatty alcohols, fatty acids (stearic acid) and waxes (paraffin wax, carnauba wax or beeswax) may also be used as fats.

Exemplary emulsifying agents according to the invention include glyceryl stearate, polysorbate 60 and the mixture of PEG-6/PEG-32/glycol stearate marketed under the trademark Tefose® 63 by Gattefosse.

Exemplary solvents according to the invention include the lower alcohols, in particular ethanol and isopropanol, and propylene glycol.

Exemplary hydrophilic gelling agents which are suitable include carboxyvinyl polymers (carbomer), acrylic copolymers such as acrylate/alkylacrylate copolymers, polyacrylamides, polysaccharides such as hydroxypropylcellulose, natural gums and clays, and, as lipophilic gelling agents, representative thereof are the modified clays such as bentones, fatty acid metal salts such as aluminum stearates and hydrophobic silica, or alternatively ethylcellulose and polyethylene.

Exemplary hydrophilic active agents which may be incorporated include proteins or protein hydrolysates, amino acids, polyols, urea, allantoin, sugars and sugar derivatives, water-soluble vitamins, starch and plant extracts, in particular Aloe vera extracts.

And exemplary lipophilic active agents include retinol (vitamin A) and derivatives thereof, tocopherol (vitamin E) and derivatives thereof, essential fatty acids, ceramides and essential oils.

It is also intended, inter alia, to combine the CGRP antagonists with active agents destined, in particular, for preventing and/or treating skin complaints, conditions and afflictions. Exemplary of these active agents are:

(1) Agents which modify cutaneous differentiation and/or proliferation and/or pigmentation such as retinoic acid and isomers thereof, retinol and esters thereof, vitamin D and derivatives thereof, estrogens such as estradiol, kojic acid or hydroquinone;

(2) Antibacterial agents such as clindamycin phosphate, erythromycin or antibiotics from the tetracycline family;

(3) Antiparasitic agents, in particular metronidazole, crotamiton or pyrethroids;

(4) Antifungal agents, in particular compounds of the imidazole family such as econazole, ketoconazole or miconazole or salts thereof, polyene compounds such as amphotericin B, compounds of the allylamine family, such as terbinafine, or alternatively octopirox;

(5) Steroidal anti-inflammatory agents such as hydrocortisone, betamethasone valerate or clobetasol propionate, or nonsteroidal anti-inflammatory agents such as ibuprofen and salts thereof, diclofenac and salts thereof, acetylsalicylic acid, acetaminophen or glycyrrhetinic acid;

(6) Anaesthetic agents such as lidocaine hydrochloride and derivatives thereof;

(7) Antipruriginous agents such as thenaldine, trimeprazine or cyproheptadine;

(8) Antiviral agents such as acyclovir;

(9) Keratolytic agents such as alpha- and beta-hydroxycarboxylic acids or beta-ketocarboxylic acids, salts, amides or esters thereof and more particularly hydroxy acids such as glycolic acid, lactic acid, salicylic acid, citric acid and fruit acids in general, and 5-n-octanoylsalicylic acid;

(10) Anti-free-radical agents such as alpha-tocopherol or esters thereof, superoxide dismutases, certain metal-chelating agents or ascorbic acid and esters thereof;

(11) Antiseborrhoeic agents such as progesterone;

(12) Antidandruff agents such as octopirox or zinc pyrithione;

(13) Antiacne agents such as retinoic acid or benzoyl peroxide.

In order to further illustrate the present invention and the advantages thereof, the following specific examples are given, it being understood that same are intended only as illustrative and in nowise limitative.

In said examples to follow, all parts and percentages are given by weight.

EXAMPLE 1

Face cream (oil-in-water emulsion):

| | |
|---|---|
| CGRP 8-37 | 0.5% |
| Glyceryl stearate | 2% |
| Polysorbate 60 (Tween 60 marketed by ICI) | 1% |
| Stearic acid | 1.4% |
| Triethanolamine | 0.7% |
| Carbomer | 0.4% |
| Cyclomethicone | 8% |
| Sunflower Oil | 12% |
| Antioxidant | 0.05% |
| Preservative | 0.3% |
| Water | qs 100% |

EXAMPLE 2

Emulsified gel (oil-in-water emulsion):

| | |
|---|---|
| Cyclomethicone | 3% |
| Purcellin oil (marketed by Dragoco) | 7% |
| PEG-6/PEG-32/glycol stearate (Tefose$^R$ 63 marketed by Gattefosse) | 0.3% |
| CGRP 8-37 | 0.0001% |
| Preservative | 0.3% |
| Carbomer | 0.6% |
| Crotamiton | 5% |
| Glycyrrhetinic acid | 2% |
| Ethyl alcohol | 5% |
| Triethanolamine | 0.2% |
| Water | qs 100% |

EXAMPLE 3

Gel:

| | |
|---|---|
| All-trans-Retinoic acid | 0.05% |
| Anti-CGRP antibody | 0.05% |
| Hydroxypropylcellulose (Klucel H marketed by Hercules) | 1% |
| Antioxidant | 0.05% |
| Isopropanol | 40% |
| Preservative | 0.3% |
| Water | qs 100% |

EXAMPLE 4

Gel:

The formulation of this example was identical to that of Example 3, except that it also contained 0.3% of sendide.

EXAMPLE 5

Cream (oil-in-water emulsion):

| | |
|---|---|
| Glyceryl stearate | 2% |
| CGRP 8-37 | 0.02% |
| Polysorbate 60 (Tween 60 marketed by ICI) | 1% |
| Stearic acid | 1.4% |
| Metronidazole | 0.5% |
| Triethanolamine | 0.7% |
| Carbomer | 0.4% |
| Cyclomethicone | 8% |
| Sunflower oil | 10% |
| Antioxidant | 0.05% |
| Preservative | 0.3% |
| Water | qs 100% |

EXAMPLE 6

Face cream (oil-in-water emulsion):

| | |
|---|---|
| Glyceryl stearate | 2% |
| Spantide | 0.5% |
| Anti-CGRP antibody | 0.02% |
| Polysorbate 60 (Tween 60 marketed by ICI) | 1% |
| Stearic acid | 1.4% |
| Triethanolamine | 0.7% |
| Carbomer | 0.4% |
| Cyclomethicone | 8% |
| Sunflower oil | 12% |
| Antioxidant | 0.05% |
| Preservative | 0.3% |
| Water | qs 100% |

EXAMPLE 7

Face cream (oil-in-water emulsion):

| | |
|---|---|
| CGRP 8-37 | 0.25% |
| Glyceryl stearate | 2.00% |
| Polysorbate 60 (Tween 60 marketed by ICI) | 1.00% |
| Stearic acid | 1.40% |
| Metronidazole | 1.00% |
| Triethanolamine | 0.70% |
| Carbomer | 0.40% |
| Liquid fraction of karite butter | 12.00% |
| Liquid petrolatum | 12.00% |
| Antioxidant | 0.05% |
| Fragrance | 0.50% |
| Preservative | 0.30% |
| Water | qs 100% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for treating at least one condition selected from the group consisting of skin redness, rosacea and discrete erythema in a subject in need of such treatment, comprising administering topically to said subject, for such period of time as is required to elicit the desired therapeutic response, a therapeutically or cosmetically effective amount of at least one CGRP antagonist.

2. The method according to claim 1, wherein said at least one CGRP antagonist comprises CGRP 8-37 or an anti-CGRP antibody.

3. The method according to claim 1, wherein said at least one CGRP antagonist is topically applied to at least one of the skin, scalp and mucous membranes.

4. The method according to claim 1, wherein the treated condition comprises skin redness of neurogenous origin.

5. The method according to claim 1, the treated condition comprises rosacea.

6. The method according to claim 1, the treated condition comprises discrete erythema.

7. The method according to claim 1, wherein said at least one CGRP antagonist is co-administered with a therapeutically effective amount of at least one antagonist of a neuropeptide other than CGRP.

8. The method according to claim 1, wherein said at least one CGRP antagonist is co-administered with a therapeutically effective amount of at least one inflammation mediator antagonist.

9. The method according to claim 1, wherein said at least one CGRP antagonist is co-administered with a therapeutically effective amount of at least one antagonist of a neuropeptide other than CGRP and at least one inflammation mediator antagonist.

10. The method according to claim 1, wherein said CGRP antagonist is co-administered with a therapeutically effective amount of at least one other agent selected from the group consisting of antibacterial agents, antiparasitic agents, anti-fungal agents, anti-inflammatory agents, antipruriginous agents, anaesthetics, antiviral agents, keratolytic agents, anti-free-radical agents, anti-seborrhoeic agents, antidandruff agents, antiacne agents, and active agents which modify at least one of cutaneous differentiation, proliferation and pigmentation.

11. The method according to claim 1, wherein said at least CGRP antagonist is co-administered with at least one other antagonist selected from the group consisting of substance P antagonists, histamine antagonists, interleukin 1 antagonists, and TNF α antagonists.

12. The method according to claim 1, wherein said at least one CGRP antagonist is co-administered with another active agent selected from the group consisting of proteins, protein hydrolysates, amino acids, polyols, allantoin, urea, sugars, sugar derivatives, vitamins, starches, plant extracts, essential fatty acids, ceramides, essential oils and hydroxy acids.

13. The method according to claim 1, wherein said at least one CGRP antagonist is administered in a pharmaceutically or cosmetically acceptable form selected from the group consisting of solutions, emulsions, microemulsions, creams, milks, foams, gels, serums, aerosols, lotions, dispersions, microcapsules, vesicles and microparticles thereof.

14. The method according to claim 1, wherein said at least one CGRP antagonist is administered in a pharmaceutically or cosmetically acceptable form selected from the group consisting of soaps, and cleansing bars.

15. The method according to claim 1, wherein said at least one CGRP antagonist is co-administered with a therapeutically effective amount of at least one substance P antagonist.

16. The method according to claim 15, wherein said at least one substance P antagonist is a substance P receptor antagonist.

17. The method according to claim 1, wherein said at least one CGRP antagonist exhibits a pharmacological response in at least one of the following tests: (a) the antagonist reduces vasodilation induced by capsaicin, (b) the antagonist induces inhibition of the release of CGRP by sensitive nerve fibers, and (c) the antagonist induces inhibition of the contraction of vas deferens smooth muscle induced by CGRP.

18. The method according to claim 11, wherein said substance P antagonist is a substance which exhibits a pharmacological response in at least one of the following two tests: (i) the antagonist decreases the extravasation of plasma across the vascular wall induced by capsaicin or by antidromic nerve stimulation, and (ii) the antagonist elicits an inhibition of the contraction of smooth muscles induced by substance P administration.

19. The method according to claim 15, wherein said substance P antagonist is a substance which exhibits a pharmacological response in at least one of the following two tests: (i) the antagonist decreases the extravasation of plasma across the vascular wall induced by capsaicin or by antidromic nerve stimulation, and (ii) the antagonist elicits inhibition of the contraction of smooth muscles induced by substance P administration.

20. The method according to claim 18, wherein said substance P antagonist elicits selective affinity for the tachykinin NK1 receptors.

21. The method according to claim 19, wherein said substance P antagonist elicits selective affinity for the tachykinin NK1 receptors.

22. The method according to claim 1, wherein said skin redness, rosacea, or discrete erythema is elicited by at least one factor selected from the group consisting of intake of food, or of hot or alcoholic drinks, rapid temperature variations, heat, exposure to ultraviolet or infrared radiation, exposure to low relative humidity, exposure of the skin to strong winds or to currents of air, exposure of the skin to surfactants, irritant dermatological topical agents, or cosmetics.

* * * * *

UNITED STATES PATENT AND TRADEMARK OFFICE
CERTIFICATE OF CORRECTION

PATENT NO. : 5,932,215
DATED : August 3, 1999
INVENTOR(S) : Olivier DE LACHARRIERE et al.

It is certified that error appears in the above-identified patent and that said Letters Patent is hereby corrected as shown below:

At Column 3, line 16, please change "induce an" to --reduce--.

Signed and Sealed this

Twenty-fourth Day of October, 2000

*Attest:*

Q. TODD DICKINSON

*Attesting Officer*      *Director of Patents and Trademarks*